US011980885B2

(12) United States Patent
Lin et al.

(10) Patent No.: US 11,980,885 B2
(45) Date of Patent: May 14, 2024

(54) TEMPERATURE CONTROL ON DIGITAL MICROFLUIDICS DEVICE

(71) Applicant: MGI Holdings Co., Limited, Guangdong (CN)

(72) Inventors: Yan-You Lin, Fremont, CA (US); Jian Gong, Danville, CA (US); Frank Zhong, Menlo Park, CA (US)

(73) Assignee: MGI Holdings Co., Limited, Shenzhen (CN)

( * ) Notice: Subject to any disclaimer, the term of this patent is extended or adjusted under 35 U.S.C. 154(b) by 0 days.

(21) Appl. No.: 18/302,183

(22) Filed: Apr. 18, 2023

(65) Prior Publication Data

US 2023/0249186 A1 Aug. 10, 2023

Related U.S. Application Data

(63) Continuation of application No. 17/004,614, filed on Aug. 27, 2020, now Pat. No. 11,660,602.

(Continued)

(51) Int. Cl.
*G01N 33/68* (2006.01)
*A01N 1/02* (2006.01)
(Continued)

(52) U.S. Cl.
CPC ........... *B01L 3/502792* (2013.01); *B01L 7/52* (2013.01); *C12Q 1/6851* (2013.01); *G01K 1/026* (2013.01);
(Continued)

(58) Field of Classification Search
CPC .. B01L 3/502792; B01L 7/52; B01L 2200/10; B01L 2200/147;
(Continued)

(56) References Cited

U.S. PATENT DOCUMENTS 6,494,616 B1 * 12/2002 Tokhtuev ................. G01D 3/02
374/E1.005
8,940,147 B1 1/2015 Bartsch et al.
(Continued)

FOREIGN PATENT DOCUMENTS

CN 109536384 A 3/2019
JP 2016539343 A 12/2016
(Continued)

OTHER PUBLICATIONS

European Application No. 20858617.2, Extended European Search Report dated Aug. 28, 2023, 8 pages.
(Continued)

*Primary Examiner* — Jennifer Wecker
*Assistant Examiner* — Oyeleye Alexander Alabi
(74) *Attorney, Agent, or Firm* — Kilpatrick Townsend & Stockton LLP

(57) ABSTRACT

A microfluidic device includes first and second substrate structures. The first substrate structure has a first substrate surface configured to receive one or more droplets. A plurality of electrodes configured to apply an electric field to the droplets. The second substrate structure has a second substrate surface facing the first substrate surface and spaced apart from the first substrate surface to form a fluid channel. The microfluidic device has a first heating element adjacent to the first substrate structure and disposed on an opposite side of the first substrate surface, and a second heating element adjacent to the second substrate structure and disposed on an opposite side of the second substrate surface. The microfluidic device further includes one or more temperature sensors disposed adjacent to the fluid channel between the first substrate structure and the second substrate structure.

6 Claims, 10 Drawing Sheets

Related U.S. Application Data

(60) Provisional application No. 62/893,091, filed on Aug. 28, 2019.

(51) Int. Cl.

| | |
|---|---|
| *B01J 19/00* | (2006.01) |
| *B01J 23/42* | (2006.01) |
| *B01L 3/00* | (2006.01) |
| *B01L 7/00* | (2006.01) |
| *C07C 309/65* | (2006.01) |
| *C07C 309/73* | (2006.01) |
| *C12Q 1/6851* | (2018.01) |
| *G01K 1/02* | (2021.01) |
| *G01N 1/40* | (2006.01) |
| *G01N 21/01* | (2006.01) |
| *G01N 21/31* | (2006.01) |
| *G01N 21/33* | (2006.01) |
| *G01N 21/35* | (2014.01) |
| *G01N 21/3504* | (2014.01) |
| *G01N 21/64* | (2006.01) |
| *G01N 27/414* | (2006.01) |
| *G01N 33/52* | (2006.01) |
| *G01N 33/532* | (2006.01) |
| *G01N 33/543* | (2006.01) |
| *G01N 33/569* | (2006.01) |
| *G01N 33/72* | (2006.01) |
| *G01N 35/00* | (2006.01) |
| *G01N 35/02* | (2006.01) |
| *G01N 35/04* | (2006.01) |
| *G01N 35/10* | (2006.01) |

(52) U.S. Cl.
CPC ..... *B01L 2200/10* (2013.01); *B01L 2200/147* (2013.01); *B01L 2300/0645* (2013.01); *B01L 2300/1827* (2013.01); *B01L 2400/0427* (2013.01); *C01B 2203/1614* (2013.01); *G01K 2217/00* (2013.01)

(58) Field of Classification Search
CPC ..... B01L 2300/0645; B01L 2300/1827; B01L 2400/0427; B01L 2300/1822; C12Q 1/6851; C12Q 1/686; G01K 1/026; G01K 2217/00; C01B 2203/1614
See application file for complete search history.

(56) References Cited

U.S. PATENT DOCUMENTS

| | | | |
|---|---|---|---|
| 11,660,602 B2 | 5/2023 | Lin et al. | |
| 2008/0131956 A1* | 6/2008 | Chung | C12Q 1/6844 435/286.1 |
| 2011/0048951 A1* | 3/2011 | Wu | B01L 3/502792 204/600 |
| 2015/0225772 A1 | 8/2015 | Li et al. | |
| 2016/0199832 A1 | 7/2016 | Jamshidi et al. | |
| 2018/0178217 A1 | 6/2018 | Jebrail et al. | |
| 2018/0264427 A1 | 9/2018 | Chu | |
| 2018/0345279 A1* | 12/2018 | Anderson | G02B 26/005 |
| 2019/0331536 A1* | 10/2019 | Hioki | H01C 7/04 |
| 2021/0241857 A1 | 8/2021 | Fraley et al. | |

FOREIGN PATENT DOCUMENTS

| | | |
|---|---|---|
| JP | 2018512884 A | 5/2018 |
| WO | 2016170109 A1 | 10/2016 |
| WO | 2018200872 A1 | 11/2018 |
| WO | 2020026200 A1 | 2/2020 |

OTHER PUBLICATIONS

International Application No. PCT/CN2020/111570, International Preliminary Report on Patentability dated Mar. 10, 2022, 5 pages.
International Application No. PCT/CN2020/111570, International Search Report and Written Opinion dated Nov. 30, 2020, 9 pages.

* cited by examiner

TEMPERATURE CONTROL ON DIGITAL MICROFLUIDICS DEVICE

CROSS-REFERENCES TO RELATED APPLICATIONS

This application claims benefit and is a continuation of application Ser. No. 17/004,614 filed Aug. 27, 2020, which claims the benefit and priority to U.S. Provisional Patent Application No. 62/893,091, filed Aug. 28, 2019, the content of all of which are incorporated in their entirety herein by reference.

FIELD OF THE INVENTION

Embodiments of the present invention relate generally to microfluidic devices, and more particularly relate to apparatus of methods for temperature control in microfluidic devices.

BACKGROUND OF THE INVENTION

A microfluidic device deals with the behavior, precise control, and manipulation of fluids that are geometrically constrained to a small, typically sub-millimeter, scale at which capillary penetration governs mass transport. Low volumes of fluids are processed to achieve multiplexing, automation, and high-throughput screening, etc. The microfluidic device can be used in DNA chips, lab-on-a-chip technology, and other technologies. In digital microfluidics, discrete, independently controllable droplets are manipulated on a substrate using electrowetting.

Electrowetting-on-dielectric (EWOD) is a liquid driving mechanism to change a contact angle of an aqueous droplet between two electrodes on a hydrophobic surface. A bulk liquid droplet as large as several microliters in volume or as small as a few nanoliters can be moved by an array of electrodes disposed on a substrate, such as an inorganic substrate (e.g., silicon/glass substrate) or organic substrate (e.g., a cyclic olefin polymer/polycarbonate substrate).

Even though microfluidic devices are finding increasing use, conventional microfluidic devices do not provide satisfactory performances, as explained further below.

BRIEF SUMMARY OF THE INVENTION

In many biology or chemistry assay workflows, such as next generation DNA sequencing library preparation, temperature control is an important parameter, which may influence the quality and quantity of the results. For most of the conventional work on assays, temperature control is usually applied to the reactions inside the droplets. However, for digital microfluidic droplets, the droplet volume size is too small to allow temperature detection directly in the droplets, and the reagent volume is too small for the temperature to be accurately (e.g., to a resolution of 1° C.) by traditional methods.

Embodiments of the present disclosure provide an apparatus, system, and method for controlling the temperature of microfluidic devices. In some embodiments, the microfluidic device has top and bottom substrates defining a fluid channel in the digital microfluidic device and TEC (thermoelectric cooler) Peltier heater beneath the target temperature control area and a resistance heater on top of the top substrate. The top heater can keep the environment temperature stable, and the bottom TEC can ramp to the temperature the assays require. One or more NTC (native temperature coefficient) thermistors are mounted to the surface on the substrate of the digital microfluidic device within the footprint of the heating area, so that the NTC can feedback the temperature to our system to adjust the power of the TEC to precisely control the temperature inside the device. For example, in some embodiments, the system can improve the temperature stability (<0.5° C.) and has real time temperature feedback.

Accordingly to some embodiments of the present invention, a microfluidic device includes a first substrate structure having a first substrate surface, and a second substrate structure having a second substrate surface facing the first substrate surface and spaced apart from the first substrate surface to form multiple fluid channels for one or more droplets between the first substrate structure and the second substrate structure. The microfluidic device also includes a plurality of electrodes adjacent to the multiple fluid channels for moving the droplets by electrowetting. The multiple fluid channels includes a first region including a first fluid channel for receiving a droplet, a second region including a second fluid channel for receiving one or more reagents, a third region in communication with the first region and the second region, the third region including a third fluid channel configured to mix the droplet with the one or more reagents to obtain a mixed droplet, and a fourth region in communication with the third region, the fourth region including a fourth fluid channel configured to process the mixed droplet. The microfluidic device further includes a first heating element and a second heating element disposed on either side, respectively, of the third region of the fluid channel. The microfluidic device can further include a third heating element and a fourth heating element disposed on either side, respectively, of the fourth region of the fluid channel.

In some embodiments of the above microfluidic device, microfluidic device is configured to perform droplet amplification in the fourth region.

In some embodiments, the fourth region includes a plurality of hydrophilic surface regions spaced apart from one another by hydrophobic surface regions, the fourth region configured to process the mixed droplet such that a portion of the droplet forms a plurality of microdroplets on the hydrophilic surface regions when the droplet moves over the hydrophilic surface regions.

In some embodiments, the fourth region comprises a hydrophobic surface region and configured for droplet digital PCR (Polymerase Chain Reaction).

In some embodiments, the first heating element and the third heating element are TEC (thermoelectric cooler) Peltier heaters, and the second heating element and the fourth heating element are resistive heaters.

In some embodiments, the first heating element and the third heating element are TEC (thermoelectric cooler) Peltier heaters, and the second heating element and the fourth heating element are TEC (thermoelectric cooler) Peltier heaters.

In some embodiments, the first heating element and the third heating element are resistive heaters, and the second heating element and the fourth heating element are resistive heaters.

In some embodiments, the first substrate structure includes a first base substrate and a first dielectric layer disposed over the first base substrate, with the first substrate surface overlying the first dielectric layer. The plurality of electrodes are disposed in the first dielectric layer.

In some embodiments, the plurality of electrodes in the first substrate structure includes a plurality of actuation electrodes, and the second substrate structure includes a second base substrate and a common electrode.

In some embodiments, the microfluidic device further includes one or more temperature sensors disposed on the first substrate surface.

In some embodiments, the microfluidic device further includes a controller configured to monitor temperature measurements provided by the one or more temperature sensors to control at least one of the first heating element and the second heating element.

In some embodiments, the each of the one or more temperature sensors includes an NTC (native temperature coefficient) thermistor.

In some embodiments, the controller is configured to determine a temperature distribution over the first substrate surface.

In some embodiments, the microfluidic device also includes one or more temperature sensors disposed on the second substrate surface.

According to some embodiments of the present invention, a microfluidic device includes a first substrate structure having a first substrate surface, at least a portion of the first substrate surface being hydrophobic, the first substrate surface configured to receive one or more droplets. The microfluidic device also includes a plurality of electrodes disposed in the first substrate structure and configured to apply an electric field to the one or more droplets. The microfluidic device also includes a second substrate structure having a second substrate surface facing the first substrate surface and spaced apart from the first substrate surface to form a fluid channel between the first substrate structure and the second substrate structure, at least a portion of the second substrate surface being hydrophobic. The microfluidic device also includes a first heating element adjacent to the first substrate structure and disposed on an opposite side of the first substrate surface, and a second heating element adjacent to the second substrate structure and disposed on an opposite side of the second substrate surface. The microfluidic device also includes one or more temperature sensors disposed adjacent to the fluid channel between the first substrate structure and the second substrate structure.

In some embodiments of the above microfluidic device, the first heating element is a TEC (thermoelectric cooler) Peltier heater, and the second heating element is a resistive heater.

In some embodiments, the first heating element is a first TEC (thermoelectric cooler) Peltier heater, and the second heating element is a second TEC (thermoelectric cooler) Peltier heater.

In some embodiments, the first heating element is a first resistive heater, and the second heating element is a second resistive heater.

In some embodiments, the first substrate structure includes a first base substrate and a first dielectric layer disposed over the first base substrate, with the first substrate surface overlying the first dielectric layer. The plurality of electrodes are disposed in the first dielectric layer.

In some embodiments, the plurality of electrodes in the first substrate structure includes a plurality of actuation electrodes. The second substrate structure includes a second base substrate and a common electrode.

In some embodiments, the microfluidic device also includes a temperature controller configured to monitor temperature measurements provided by the one or more temperature sensors to control at least one of the first heating element and the second heating element.

In some embodiments, the each of the one or more temperature sensors includes an NTC (native temperature coefficient) thermistor.

In some embodiments, the controller is configured is configured to determine a temperature distribution over the first substrate surface using a plurality of temperature sensors distributed on the first substrate surface.

In some embodiments, the microfluidic device also includes one or more temperature sensors disposed on the second substrate surface in the space between the first substrate structure and the second substrate structure.

According to some embodiments of the present invention, a method for controlling the temperature of a microfluidic device includes providing a first substrate structure and a second substrate structure, the first substrate structure having a first substrate surface and the second substrate structure having a second substrate surface, the second substrate surface facing the first substrate surface and spaced apart from the first substrate surface by a distance to form a fluid channel for one or more droplets. The method also includes determining fluid channel temperature from one or more temperature sensors disposed on the first substrate surface, and controlling the temperature of the fluid channel. In the method, controlling the temperature of the fluid channel includes controlling a first heating element disposed adjacent to the first substrate surface based on the fluid channel temperature in the fluid channel, and controlling a second heating element disposed adjacent to the second substrate surface based on the fluid channel temperature in the fluid channel.

In some embodiments of the above method, the each of the one or more temperature sensors comprises an NTC (native temperature coefficient) thermistor.

In some embodiments, the first heating element is a TEC (thermoelectric cooler) Peltier heater, and the second heating element is a resistive heater.

In some embodiments, the first heating element is a first TEC (thermoelectric cooler) Peltier heater, and the second heating element is a second TEC (thermoelectric cooler) Peltier heater.

In some embodiments, controlling the temperature of the fluid channel includes:
controlling the first heating element to heat the fluid channel to a first temperature for a first time duration for droplet amplification;
controlling the first heating element to heat the fluid channel at a second temperature for a second time duration for droplet annealing; and
setting the second heating element at a preset constant third temperature.

In some embodiments, each of the one or more temperature sensors comprises an NTC (native temperature coefficient) thermistor.

In some embodiments, the method also includes sensing temperature of the fluid channel using one or more temperature sensors disposed on the second substrate surface in the fluid channel.

In some embodiments, the method also includes a temperature controller configured to monitor temperature measurements provided by the one or more temperature sensors to control at least one of the first heating element and the second heating element.

The following description, together with the accompanying drawings, provides further description of the nature and advantages of the claimed invention.

BRIEF DESCRIPTION OF THE DRAWINGS

FIG. 3A is a simplified top view illustrating that a droplet is discharged on a first electrode of an array of electrodes according to an embodiment of the present disclosure.

FIG. 3B is a simplified top view illustrating that the droplet is moved to a second (adjacent) electrode under the effect of electric fields by the microfluidic device according to an embodiment of the present disclosure.

FIG. 3C is a simplified top view illustrating that the droplet is moved out of the array of electrodes while leaving a residue on the second electrode according to an embodiment of the present disclosure.

In accordance with common practice, the described features and elements are not drawn to scale, but are drawn to emphasize features and elements relevant to the present disclosure.

DETAILED DESCRIPTION OF THE INVENTION

Figure 1A:
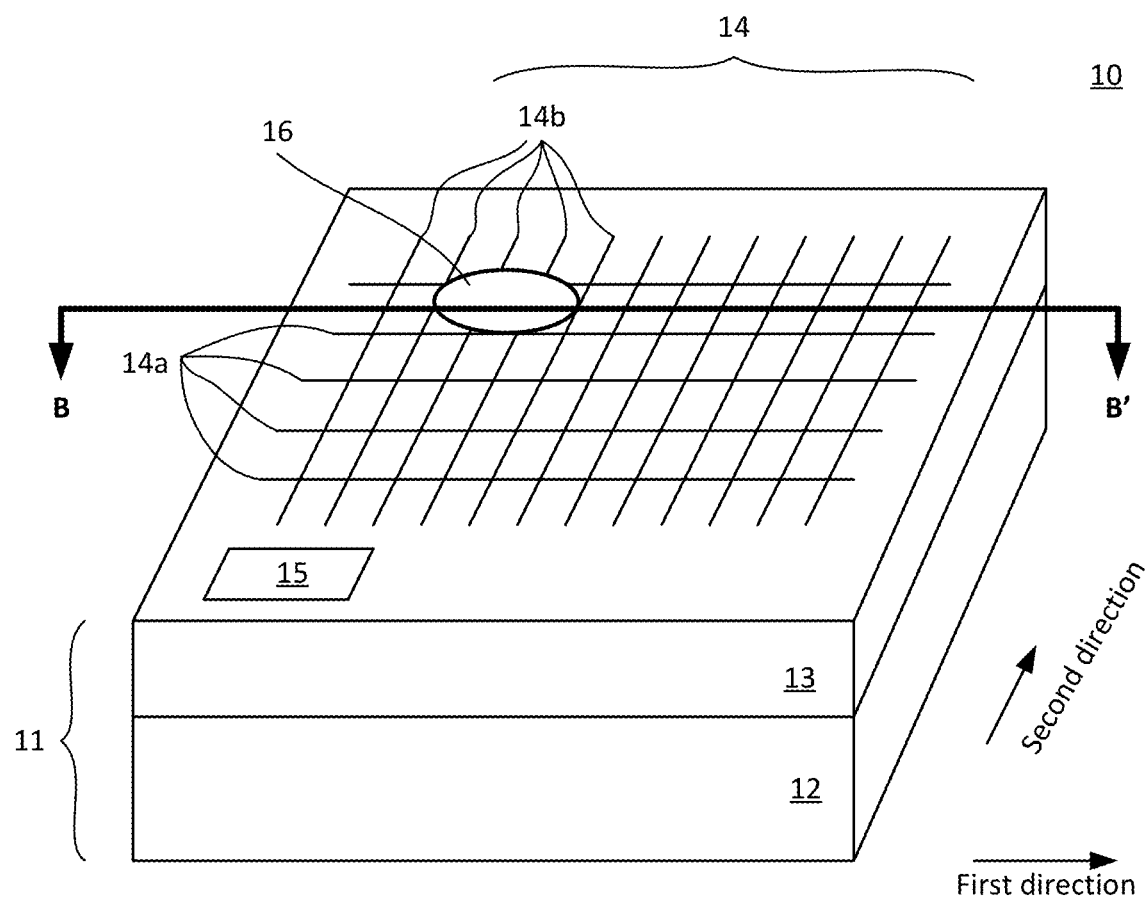
FIG. 1A is a simplified perspective view of a schematic diagram illustrating a microfluidic device according to some embodiments of the present disclosure.

FIG. 1A is a perspective view of a schematic diagram illustrating a portion of a microfluidic device 10 according to some embodiments of the present disclosure. The microfluidic device 10 includes a substrate structure 11 having a substrate 12, an insulating layer 13 on the substrate, and an array of electrodes 14 within or under the insulating layer. The array of electrodes 14 includes a first set of electrodes 14a arranged in parallel to each other and spaced apart from each other in a first direction, and a second set of electrodes 14b arranged in parallel to each other and spaced apart from each in a second direction substantially perpendicular to the first direction. The first and second set of electrodes are spaced apart from each other within the insulating layer 13, which may include a plurality of dielectric layers of the same material or different materials. The microfluidic device also includes an input-output circuit 15 in the substrate and operative to interface with an external control circuit to provide control voltages having time-varying voltage waveforms to the array of electrodes 14.

Referring to FIG. 1A, a liquid droplet 16 is disposed on the surface of the insulating layer 13, and may be moved along a certain direction by turning off/off control voltages at the electrodes below the droplet and at adjacent electrodes.

Figure 1B:
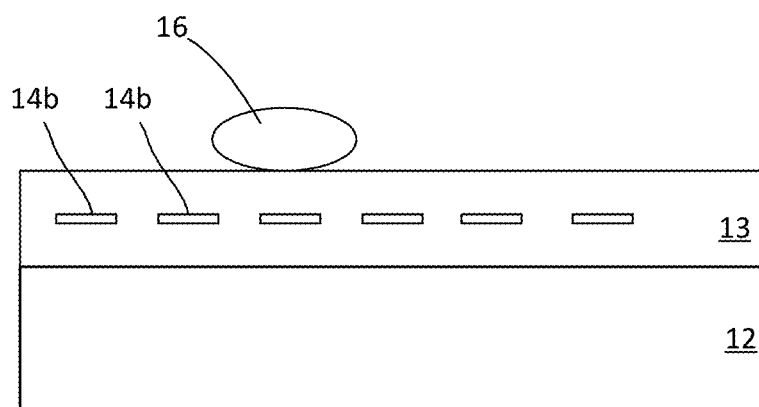
FIG. 1B is a simplified cross-sectional view of the microfluidic device shown in FIG. 1A taken along the line B-B'.

FIG. 1B is a cross-sectional view of the microfluidic device 10 shown in FIG. 1A taken along a cut line B-B'. The cross sectional view of the second set of electrodes 14b is shown in FIG. 1B. The first set of electrodes 14a (not shown) may be disposed above or below the second set of electrodes 14b and spaced apart from the second set of electrodes by one or more dielectric layers.

Figure 2A:
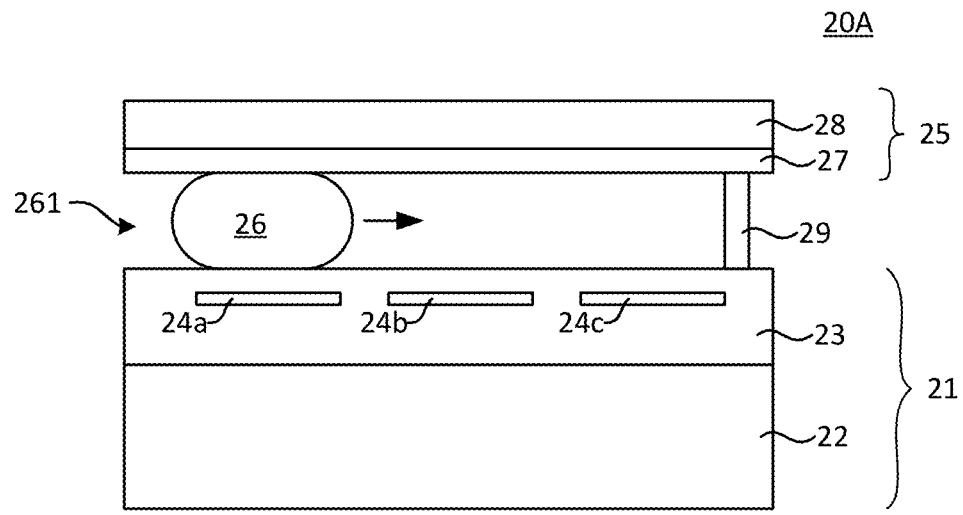
FIG. 2A is a simplified cross-sectional view of a portion of a microfluidic device according to an embodiment of the present disclosure.

FIG. 2A is a simplified cross-sectional view of a portion of a microfluidic device 20A according to an embodiment of the present disclosure. Referring to FIG. 2A, the microfluidic device 20A includes a first substrate 22, a dielectric layer 23 on the substrate 21, a set of actuation electrodes 24 (e.g., 24a, 24b, 24c) within the dielectric layer 23, a common electrode 27 attached to a second substrate 28 and facing toward the actuation electrodes 24. The common electrode 27 may be grounded or have another common voltage. The dielectric layer 23 and the common electrode 27 are spaced apart from each other by a spacer 29. Referring to FIG. 2A, a droplet 26 is disposed between the actuation electrodes 24 and the common electrode 27 and is moving along a lateral direction across the surface of the dielectric layer 23 by means of changing or varying the voltage levels applied to the actuation electrodes in relation to the common electrode. In an embodiment, the microfluidic device 20A may further include a control circuit (not shown) configured to provide control voltages to the common electrode and the actuation electrodes. By turning on and off voltages applied to the actuation electrodes, the control circuit can move the droplet 26 in a lateral direction across the surface of the dielectric layer 23. For example, an electric field is generated by applying a first voltage to the actuation electrode 24a below the droplet 26 and a second voltage to the adjacent actuation electrode 24b, the generated electric field causes the droplet 26 to move toward the actuation electrode 24b. The moving speed of the droplet 26 can be controlled by the magnitude of a voltage difference between the adjacent actuation electrodes. In an embodiment, the form of the droplet 26 can be changed by varying the voltage difference between the actuation electrodes 24 and the common electrode 27 where the droplet 26 is disposed therebetween. It is understood that the number of actuation electrodes in the set of actuation electrodes can be any integer number. In the example shown in FIG. 2A, three actuation electrodes are used in the set of actuation electrodes. But it is understood that the number is arbitrarily chosen for describing the example embodiment and should not be limiting.

Referring to FIG. 2A, the two substrate structures may be separately formed. For example, a first substrate structure 21 may be formed including the substrate 22, the dielectric layer 23, and the actuation electrodes 24 within the dielectric layer 23. The substrate 22 may be a thin-film transistor (TFT) array substrate formed by conventional thin-film transistor manufacturing processes. A second substrate structure 25 may include a substrate 28 and a common electrode layer 27 on the substrate 28. There can be a dielectric layer (not shown) under the common electrode for contact with the droplet. A spacer 29 may be formed either on the first substrate structure or the second substrate structure. In certain embodiments, the spacer 29 has a height in the range between several micrometers to several millimeters. In general, the height of the spacer 29 is less than the diameter of the droplet such that the droplet disposed on the dielectric layer 23 has physical contact with the second substrate structure. The first and second substrate structures are then bonded together to form the microfluidic device 20A. In other words, the space or air gap between the first substrate structure and the second substrate structure is determined by the height or thickness of the spacer 29. The space or air gap forms a fluid channel 261 for the droplets.

In the embodiment shown in FIG. 2A, the common electrode 27 and the set of actuation electrodes 24 (e.g., 24a, 24b, 24c) are connected to voltages provided by a control circuit (not shown) through the input-output circuit 15 shown in FIG. 1A. In some embodiments, the common electrode may be connected to a ground potential or a stable DC voltage. The control circuit applies time varying voltages through the input-output circuit to the set of actuation electrodes through respective electronic switches (that can be, e.g., thin film transistors or MOS circuitry in the substrate or off-chip) to generate an electric field across the droplet to move the droplet along a path. In some embodiments, the surface of the common electrode 27 is covered by an insulating layer made from a hydrophobic material. In other embodiments, the surface of the dielectric layer 23 is coated with a thin hydrophobic film having a submicron thickness.

Figure 2B:
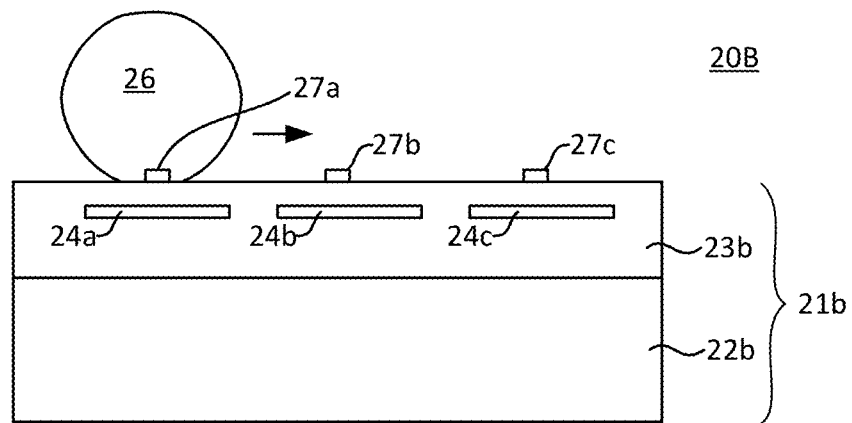
FIG. 2B is a simplified cross-sectional view of a portion of a microfluidic device according to another embodiment of the present disclosure.

FIG. 2B is a simplified cross-sectional view of a portion of an microfluidic device 20B according to another embodiment of the present disclosure. Referring to FIG. 2B, the microfluidic device 20B includes a substrate 22b, a dielectric layer 23b on the substrate 21b, a set of actuation electrodes 24 (24a, 24b, 24c) within the dielectric layer 23b, and a set of common electrodes 27 (e.g., 27a, 27b, and 27c) overlying the dielectric layer 23b. The common electrode 27b and the actuation electrodes are spaced apart from each other by a portion of the dielectric layer. Similar to FIG. 2A, the droplet 26 can be moved along a path in the lateral direction across the surface of the dielectric layer 23b by applying a first voltage at the actuation electrode (e.g., 24a) below the droplet 26 and a second voltage at the adjacent actuation electrode (e.g., 24b). The movement and direction of the droplet 26 is thus controlled by the control circuit (not shown) which applies voltages to certain actuation electrodes through a set of electronic switches (MOS circuitry in the substrate 22b, not shown). Different to the microfluidic device 20A shown in FIG. 20A, the microfluidic device 20B has the common electrode 27a close to the actuation electrodes 24, and the droplet 26 is not sandwiched between the common electrode 27 and the actuation electrodes 24. The microfluidic device 20B also differs from the microfluidic 20A by not having the spacer 29.

Referring to FIG. 2B, the set of actuation electrodes 24 and the set of common electrodes 27 may be two layers of strip electrodes intersected with each other on different planes on the substrate. The actuation electrodes 24 and the common electrodes 27 are operative to move the droplet 26 across the surface of the dielectric layer 23b. In some embodiments, the common electrode 27b has a surface that is covered by an insulating layer made from a hydrophobic material. In other embodiments, the surface of the dielectric layer 23 is coated with a thin hydrophobic film having a submicron thickness.

Figure 2C:
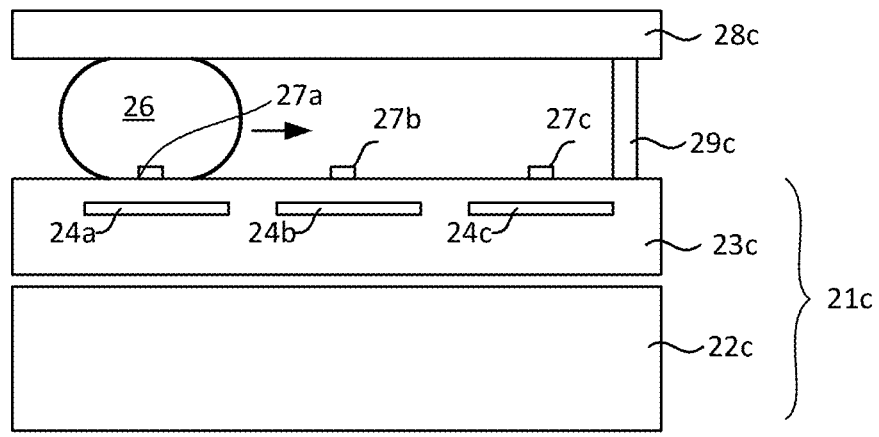
FIG. 2C is a simplified cross-sectional view of a portion of a microfluidic device according to yet another embodiment of the present disclosure.

FIG. 2C is a cross-sectional view of a portion of a microfluidic device 20C according to yet another embodiment of the present disclosure. Referring to FIG. 2C, the microfluidic device 20C includes a substrate structure 21c including a substrate 22c, a dielectric layer 23c on the substrate 22c, and a set of actuation electrodes 24 (e.g., 24a, 24b, and 24c) within the dielectric layer 23c. A set of common electrodes 27 (e.g., 27a, 27b, and 27c) are formed overlying the dielectric layer 23c. The common electrode 27c and the actuation electrodes are spaced apart from each other by a portion of the dielectric layer. In some embodiments, the common electrode 27a has a surface that is covered by an insulating layer made from a hydrophobic material or a thin film of submicron hydrophobic coating on the surface of dielectric layer 23. The microfluidic device 20C may further include a second substrate 28c spaced apart from the substrate structure 21c through a spacer 29c. Similar to FIG. 2A, the droplet 26 can be moved along a path within the channel formed by a space or air gap between the surface of the dielectric layer and the second substrate 28c. The movement of the droplet is controlled by voltages applied to the electrodes through electronic switches by a control circuit (not shown).

Figure 2D:
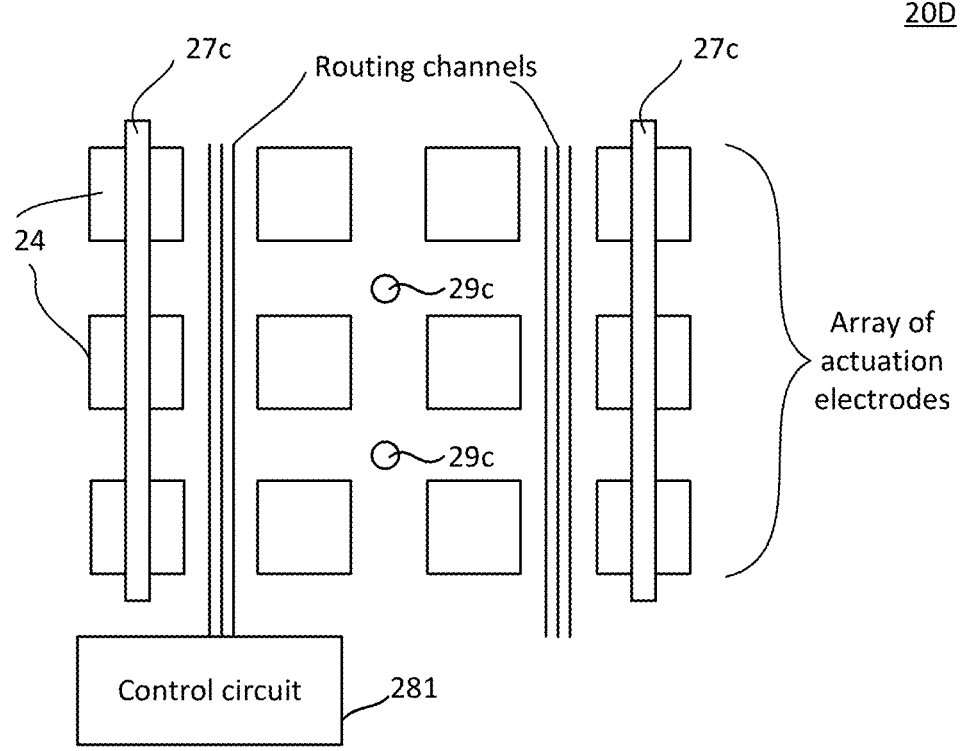
FIG. 2D is a simplified plan view of a microfluidic device according to an exemplary embodiment of the present disclosure.

FIG. 2D is a simplified plan view of a microfluidic 20D according to an exemplary embodiment of the present disclosure. Referring to FIG. 2D, the actuation electrodes 24 are arranged in an array having routing channels for routing electrical signals from a control circuit 281 to the actuation electrodes 24 and to the common electrodes 27c. The spacer 29c is shown to have a circular cross-section; however, the circular cross-sectional shape is not limiting and any other cross-sectional shapes are equally suitable such as square, rectangular, oval, elliptic, and other shapes. Similarly, the actuation electrodes are shown to have a square shape, but the square shape is not limiting and other shapes are equally suitable such as rectangular, circular, oval, elliptic and other shapes. In one embodiment, the spacer 29c is spaced at a distance to leave sufficient space to allow free movement of the droplet. In order words, the spacer 29c is dimensioned and spaced in such a way that it does not hinder movements of the droplet across the surface of the dielectric layer. It will be understood that although the routing channels are shown as coplanar with the array of electrodes, one of skill in the art will appreciate that the routing channels and the control circuit can be disposed in the substrate and in different layers of the dielectric layer. It will also be understood that the actuation electrodes 24 and the common electrodes 27c can have their relative positions transposed, i.e., the common electrodes may be disposed below the actuation electrodes.

In another embodiment, the microfluidic device may have a single array of electrodes. In other words, the common electrodes and the actuation electrodes are coplanar, i.e., the common electrodes and the actuation electrodes are arranged in a same plane within the dielectric layer. For example, a plurality of actuation electrodes and a plurality of common electrodes are arranged alternatively adjacent to each other, the control circuit may apply DC or AC voltages and ground potential sequentially to the actuation electrodes and common electrodes to control the movement of the droplet. In yet another embodiment, each electrode in the array of electrodes is individually controlled by a control circuit through a set of electronic switches such that each electrode can be an actuation electrode at a first time period and a common electrode at a second time period.

Figure 3A:
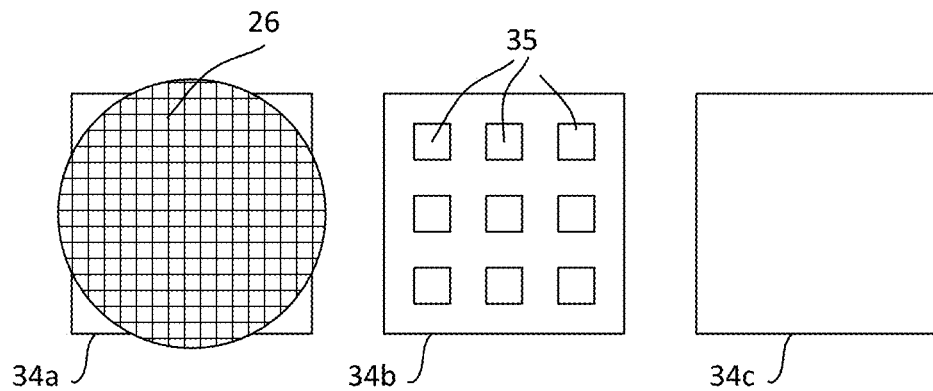
FIGS. 3A to 3C are simplified top views of a droplet moving across a surface of a dielectric layer according to embodiments of the present disclosure.
Figure 3B:
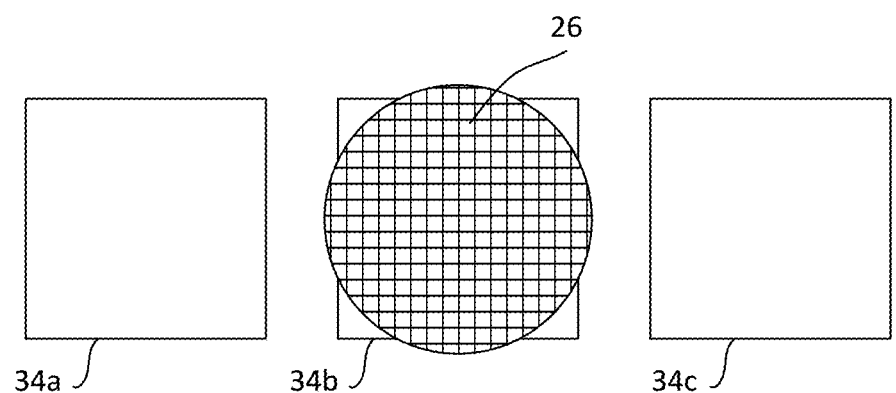
Figure 3C:
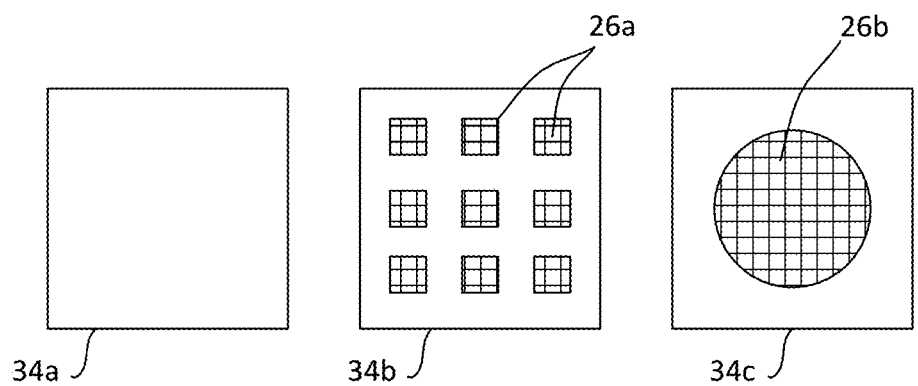

FIGS. 3A to 3C are top views of a droplet moving sequentially across a surface of a dielectric layer according to an embodiment of the present disclosure. Referring to FIG. 3A, a droplet 26 is disposed on a microfluidic device as described above in any of the microfluidic devices 20A, 20B, and 20C. The microfluidic device includes a substrate having an array of thin-film transistors or MOS circuitry, a dielectric layer on the substrate, and an array of actuation electrodes (and/or common electrodes) within the dielectric layer, the actuations electrodes and the common electrodes are connected to a control circuit through conductive wirings in the routing channels and receive control signals from the control circuit via the thin-film transistors. The droplet 26 is disposed on a surface of the dielectric layer above a first actuation electrode 34a. By turning off (or floating) the first actuation electrode below the droplet and turning on the actuation electrode next to it, the droplet can be moved toward the next electrode. In one embodiment, the surface portion of the dielectric layer above the array of the actuation electrodes can be modified with a predefined feature which has more attraction to a liquid (e.g., the liquid droplet) than a hydrophobic surface, e.g., surrounding the features. The feature may have a dimension ranging from micrometers to nanometers corresponding to microliters and nanoliters in volume, respectively. The feature 35 may be manufactured on the dielectric layer accurately thousands or million times on the dielectric layer using currently available submicron semiconductor manufacturing processes.

As used herein, turning off an actuation electrode refers to lowering the voltage of that actuation electrode to a level the same as a common voltage which is applied to the common electrode. Conversely, turning on an actuation electrode refers to increasing the voltage of that actuation electrode to a level above the common voltage. The microfluidic devices can operate with DC (DC electrowetting) or AC (AC electrowetting) voltages as long as a potential between the electrodes is at a DC voltage level to form an electric field for moving the droplet. In certain embodiments, when an adjacent electrode is completely or partially turned on, the droplet disposed adjacent to it will be moved onto that turned-on electrode and wets the features disposed on the turned-on electrode. As used herein, the term "feature" refers to a region or a structure in or on which a liquid material (e.g., a drop) is deposited or formed. By moving the droplet to a next turned-on electrode using a time-varying voltage waveform provided by a control circuit, the droplet will move from electrode to electrode, thereby leaving residual tiny drops (very small or tiny drops or microdroplets) 26a in or on the features. The volume of the residual tiny drops is completely determined by the feature dimension (size) as well as the contact angle of the liquid droplet on the surface in the environment (e.g., air or oil).

FIG. 3B is a top view illustrating that the droplet 26 is moving from the first electrode 34a to the second electrode 34b having nine features 35 according to an embodiment of the present disclosure.

FIG. 3C is a top view illustrating that the remaining droplet 26b is moving from the second electrode to the third electrode 34c, thereby leaving residual tiny drops (microdroplets) 26a in or on the features, in accordance with an embodiment of the present disclosure. To prevent evaporation of microdroplets in the air, the droplet can be surrounded by other immiscible liquid like silicone oil. It is understood that the number of features on the electrode can be any integer number. In the example shown in FIGS. 3A to 3C, nine features are used in the second electrode. But it is understood that the number is arbitrarily chosen for describing the example embodiment and should not be limiting. It is also understood that each electrode (e.g., first, second, third electrodes) may have the same number of features, or they may have different number of features. Referring to FIGS. 3A to 3C, the features are shown to have a square shape, however, it in understood the shown shape is not limiting and any other shapes are equally suitable such as circular, rectangular, oval, elliptic, polygonal, and other shape.

It is noted that the electrodes according to embodiments of the present disclosure can be arranged in various configurations and the electrodes can have many shapes. For example, the electrodes can have a polygonal shape (e.g., square, rectangular, triangular, and the like), a circular shape, an oval shape, etc. The configuration can be a checker-board configuration, or other geometric configurations.

In accordance with the present disclosure, the large number of microdroplets having a uniform size can be used to perform droplet digital PCR (Polymerase Chain Reaction) on a microfluidic chip. With a small volume of each sample and below certain DNA concentration meeting the Poisson distribution requirement, each sample of the droplet (microdroplet) would have either one DNA molecule or no DNA molecules. By thermo-cycling the samples (microdroplets) with a conventional PCR or incubating them under a certain temperature with an isothermal PCR, a single DNA molecule within a target region can be amplified on each sample within the environment (e.g., oil). After reading the final droplet's DNA concentration by optical detection or pH measurement through integrated on-chip ion-sensitive field-effect transistor (ISFET) sensors, the absolute numbers of a targeted DNA in the array of samples (microdroplets) can be quantified and then use the absolute DNA quantification to calculate the DNA concentration in the bulk droplet. The terms "sample," "residual small droplet," "small portions of the droplet," and "microdroplet" are used interchangeably herein and refer to a small droplet formed from a bulk droplet according to embodiments of the present disclosure.

In accordance with the present disclosure, a droplet containing multiple different DNA targets can be dispensed on a region of a single microfluidic chip, the droplet is then moved by electrowetting to a next region which produces a multitude of samples (copies of the DNA targets) from the droplet for detection or measurement of the samples. Further details can be found in PCT Patent Application No. PCT/IB2019/056588, filed Aug. 1, 2019, which is incorporated herein by reference.

Embodiments of the present invention further provide a novel method to control and measure the temperature inside the microfluidic device, such as a digital microfluidic cartridge. In some embodiments, the microfluidic device has the top and bottom plates of hydrophobic surface with the droplet sandwiched between them.

Figure 4:
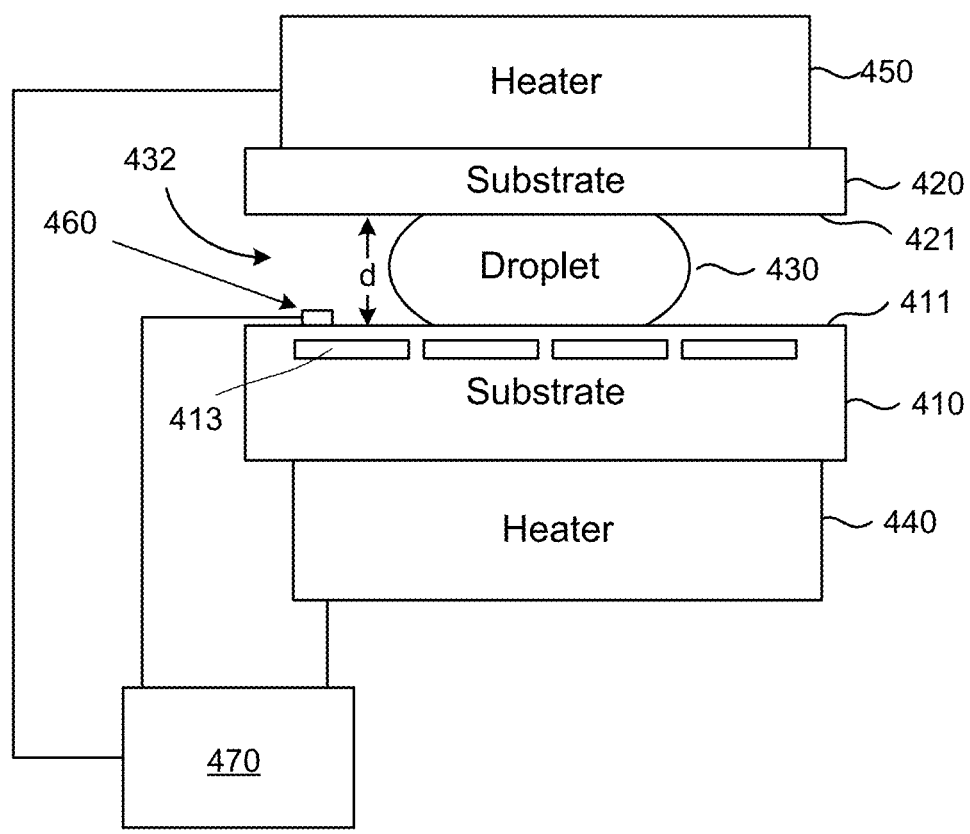
FIG. 4 is a simplified cross-sectional view of a portion of a microfluidic device according to an embodiment of the present disclosure.

FIG. 4 is a simplified cross-sectional diagram illustrating a portion of a microfluidic device for temperature sensing and control according to some embodiments of the present invention. As shown in FIG. 4, a microfluidic device 40 includes a first substrate structure 410 and a second substrate structure 420. The first substrate structure 410 has a first substrate surface 411. In some embodiments, at least a portion of the first substrate surface is hydrophobic. The first substrate surface 411 is configured to receive one or more droplets 430. A plurality of electrodes 413 are disposed in the first substrate structure 410 and configured to apply an electric field to the one or more droplets. The second substrate structure 420 has a second substrate surface 421 facing the first substrate surface 411 and spaced apart from the first substrate surface 411 by a distance "d" to define a fluid channel 432 in the space between the first substrate structure 410 and the second substrate structure 420. The distance "d" is configured to contain the one or more droplets disposed in the space as needed. In some embodiments, at least a portion of the second substrate surface 421 is hydrophobic.

Microfluidic device 40 also includes a first heating element 440 adjacent to the first substrate structure 410 and disposed on an opposite side of the first substrate surface 411. Microfluidic device 40 also includes a second heating element 450 adjacent to the second substrate structure 420 and disposed on an opposite side of the second substrate surface 421. Microfluidic device 40 can also have one or more temperature sensors 460 disposed on the first substrate surface 411 in the fluid channel 432 in the space between the first substrate structure 410 and the second substrate structure 420. Microfluidic device 40 can also include a temperature controller 470 configured to control the temperature of the fluid channel.

Figure 5:
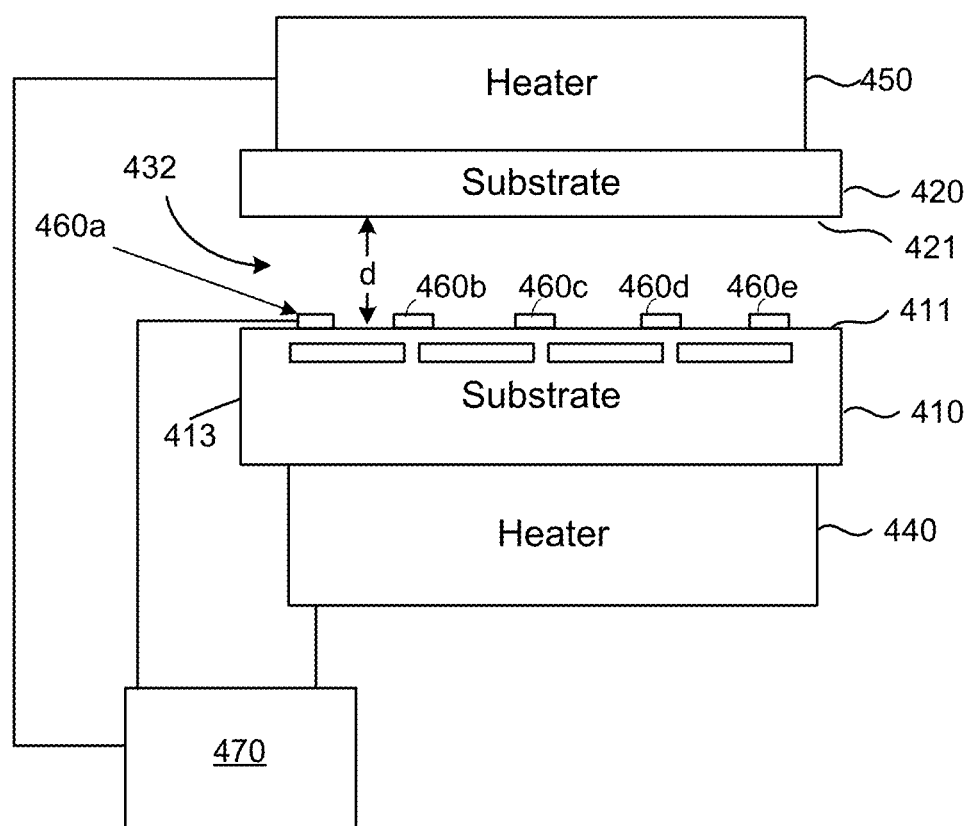
FIG. 5 is a simplified cross-sectional view of a portion of a microfluidic device according to an embodiment of the present disclosure.

FIG. 5 is a simplified cross-sectional diagram illustrating a portion of a microfluidic device for temperature sensing and control according to some embodiments of the present invention. As shown in FIG. 5, microfluidic device 50 is similar to microfluidic device 40 of FIG. 4. The common components are designated with the same reference numerals. One difference is that microfluidic device 50 has a plurality of temperature sensors 460 (e.g., 460a, 460b, 460c, 460d, and 460e, etc.) disposed on the first substrate surface 411 and distributed over the first substrate surface 411.

As shown in FIG. 5, microfluidic device 50 includes a first substrate structure 410 and a second substrate structure 420. The first substrate structure 410 has a first substrate surface 411. In some embodiments, at least a portion of the first substrate surface is hydrophobic. The first substrate surface 411 is configured to receive one or more droplets (not shown). A plurality of electrodes 413 are disposed in the first substrate structure 410 and configured to apply an electric field to the one or more droplets. The second substrate structure 420 has a second substrate surface 421 facing the first substrate surface 411 and spaced apart from the first substrate surface 411 by a distance "d" to define a fluid channel 432 in the space between the first substrate structure 410 and the second substrate structure 420. The distance "d" is configured to contain the one or more droplets disposed in fluid channel 432. In some embodiments, at least a portion of the second substrate surface 421 is hydrophobic.

Microfluidic device 50 also includes a first heating element 440 adjacent to the first substrate structure 410 and disposed on an opposite side of the first substrate surface 411. Microfluidic device 40 also includes a second heating element 450 adjacent to the second substrate structure 420 and disposed on an opposite side of the second substrate surface 421.

As described above, microfluidic device 50 can also have a plurality temperature sensors 460a, 460b, 460c, 460d, 460e, etc. disposed on the first substrate surface 411 in the space between the first substrate structure 410 and the second substrate structure 420.

In some embodiments of microfluidic devices 40 and 50, the first heating element 440 can be a TEC (thermoelectric cooler) Peltier heater, and the second heating element 450 can be a resistive heater. Thermoelectric cooling uses the Peltier effect to create a heat flux at the junction of two different types of materials. A Peltier cooler, heater, or thermoelectric heat pump is a solid-state active heat pump which transfers heat from one side of the device to the other, with consumption of electrical energy, depending on the direction of the current. The device has two sides, and when a DC electric current flows through the device, it brings heat from one side to the other, so that one side gets cooler while the other gets hotter. The "hot" side is attached to a heat sink so that it remains at ambient temperature, while the cool side goes below room temperature. In some applications, multiple coolers can be cascaded together for a lower temperature. Such an instrument is also called a Peltier device, Peltier heat pump, solid state refrigerator, or thermoelectric cooler (TEC). It can be used either for heating or for cooling. It can also be used as a temperature controller that either heats or cools.

In some embodiments both the first heating element 440 and the second heating element 450 can be TEC (thermoelectric cooler) Peltier heaters. In these embodiments the first heating element 440 can be a first TEC (thermoelectric cooler) Peltier heater, and the second heating element 450 can be a second TEC (thermoelectric cooler) Peltier heater. In some embodiments both the first heating element 440 and the second heating element 450 can be resistive heaters. In this case, the first heating element 440 can be a first resistive heater and the second heating element can be a second resistive heater.

A resistive heater can have heating elements that are formed of metal or polysilicon wires, metal or polysilicon layer(s), polysilicon layer(s) that can convert an electric energy of signals received from the control circuit 68 into a thermal energy. These resistive heating elements can be fabricated in the substrate structures using standard integrated circuit processing technologies.

In some embodiments, the digital microfluidic device can have a top and bottom substrates, and a TEC (thermoelectric cooler) Peltier heater beneath the target temperature control area and a resistance heater on top of the top substrate. The top heater can keep the environment temperature stable, and the bottom TEC can ramp to the temperature the assays require. An NTC (native temperature coefficient) thermistor is mounted to the surface on the substrate of the digital microfluidic device within the footprint of heating area, so that the NTC can feedback the temperature to the controller to adjust the power of the TEC to precisely control the temperature inside the device.

In some embodiments, similar to microfluidic devices described above in connection with FIGS. 1A-1B and 2A-2C, in microfluidic devices 40 and 50, the first substrate structure 410 can have a first base substrate and a first dielectric layer disposed over the first base substrate, with the first substrate surface overlying the first dielectric layer, and the plurality of electrodes are disposed in the first dielectric layer. To simplify the drawings, a first base substrate and a first dielectric layer are not shown in FIGS. 4 and 5.

In some embodiments, the plurality of electrodes 413 in the first substrate structure 410 can include a plurality of actuation electrodes for manipulating the droplets. Further, similar to microfluidic devices described above in connection with FIGS. 1A-1B and 2A-2C, in microfluidic devices 40 and 50, the second substrate structure 420 can include a second base substrate and a common electrode (not shown in FIGS. 4 and 5). Moreover, the common electrodes and be disposed on or in the first substrate structure 410. In the examples described herein, the actuation electrodes are disposed under the droplets. However, in some embodiments, the actuation electrodes can be disposed above the droplets.

In some embodiments, microfluidic devices 40 and 50 can also include a temperature controller 470 configured to monitor temperature measurements provided by the one or more temperature sensors 460 (or 460a-460e, etc.) to control at least one of the first heating element 440 and the second heating element 450. In some embodiments, the controller 470 is configured to determine a temperature distribution over the first substrate surface 411 using the plurality of temperature sensors, 460a-460e, etc., distributed on the first substrate surface.

The microfluidic devices 40 and 50 show temperature sensors on the surface of the first substrate. In other embodiments, a microfluidic device can have one or more temperature sensors disposed on the second substrate surface in the space between the first substrate structure and the second substrate structure.

In some embodiments, each of the one or more temperature sensors 460 (or 460a-460e, etc.) can be an NTC (native temperature coefficient) thermistor. NTC thermistors are resistors with a negative temperature coefficient, which means that the resistance decreases with increasing temperature. The temperature sensitivity coefficient is about five times greater than that of silicon temperature sensors (silistors) and about ten times greater than those of resistance temperature detectors (RTDs). NTC sensors are typically used in a range from −55° C. to 200° C. NTC thermistors are generally made of ceramics or polymers. Different materials used result in different temperature responses, as well as other characteristics. For example, many NTC thermistors are made from a pressed disc, rod, plate, bead or cast chip of semiconducting material, such as sintered metal oxides. They work because raising the temperature of a semiconductor increases the number of active charge carriers in the conduction band.

In some embodiments, off-the-shelf NTC thermistors can be disposed in a microfluidic device. Alternatively, thin film NTC thermistors can be fabricated on the substrate structures in the microfluidic device.

In some embodiments, multiple NTC thermistors or resistive heaters are disposed on the surface within a heating area to demonstrate the temperature distribution is uniform across the fluid channel, so that one NTC read out in the heating zone can stand for the whole area.

Figure 6A:
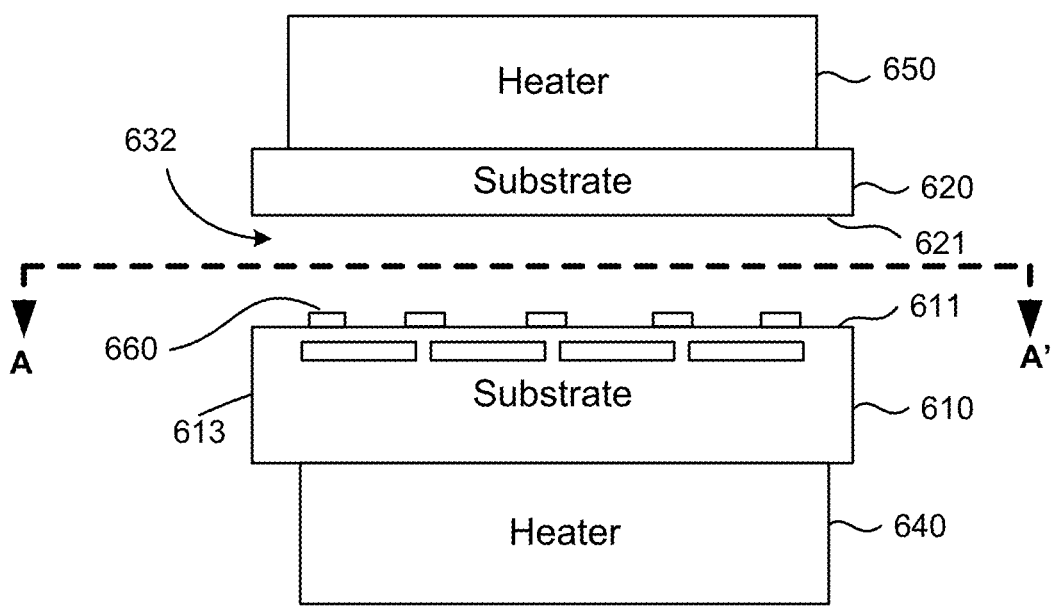
FIG. 6A is a simplified cross-sectional view of a microfluidic device configured as an integrated lab-on-a-chip device according to an embodiment of the present disclosure.

FIG. 6A is a simplified cross-sectional view of a microfluidic device configured as an integrated lab-on-a-chip device according to an embodiment of the present disclosure. As shown in FIG. 6A, microfluidic device 60A is similar to microfluidic device 50 of FIG. 5. Microfluidic device 60A includes a first substrate structure 610 and a second substrate structure 620. The first substrate structure 610 has a first substrate surface 611. In some embodiments, at least a portion of the first substrate surface is hydrophobic. The first substrate surface 611 is configured to receive one or more droplets (not shown). The second substrate structure 620 has a second substrate surface 621 facing the first substrate surface 611 and spaced apart from the first substrate surface 611 to define one or more fluid channel 632 in the space between the first substrate structure 610 and the second substrate structure 620. The one or more fluid channel 632 is configured to contain the one or more droplets. In some embodiments, at least a portion of the second substrate surface 621 is hydrophobic. A plurality of actuation electrodes 613 are disposed in the first substrate structure 610 adjacent to the one or more fluid channels 632 and configured to apply an electric field for moving the one or more droplets by electrowetting. For simplicity, the common electrodes are omitted in FIG. 6A. In the example of FIG. 6A, the actuation electrodes 613 are shown to be in the first substrate structure 610 underlying the fluid channels 632. Alternatively, the actuation electrodes can be disposed on the first substrate surface in the fluid channels. In some embodiments, the actuation electrodes can be disposed above the fluid channels. For example, in FIG. 6B, the actuation electrodes 613 can be disposed in the second substrate 620 or on the second substrate surface 621.

Microfluidic device 60A also includes a first heating element 640 adjacent to the first substrate structure 610 and disposed on an opposite side of the first substrate surface 611. Microfluidic device 60 also includes a second heating element 650 adjacent to the second substrate structure 620 and disposed on an opposite side of the second substrate surface 621.

As described above, microfluidic device 60A can also have a plurality temperature sensors 660 disposed on the first substrate surface 611 in the space between the first substrate structure 610 and the second substrate structure 620.

In some embodiments, microfluidic device 60A can be configured as an integrated lab-on-a-chip device including different regions for droplet processing. An example of integrated lab-on-a-chip device is illustrated in FIG. 6B, which shows a top plan view of a microfluidic device along a plane at cutline A-A' in the one or more fluid channel 632 in FIG. 6A.

Figure 6B:
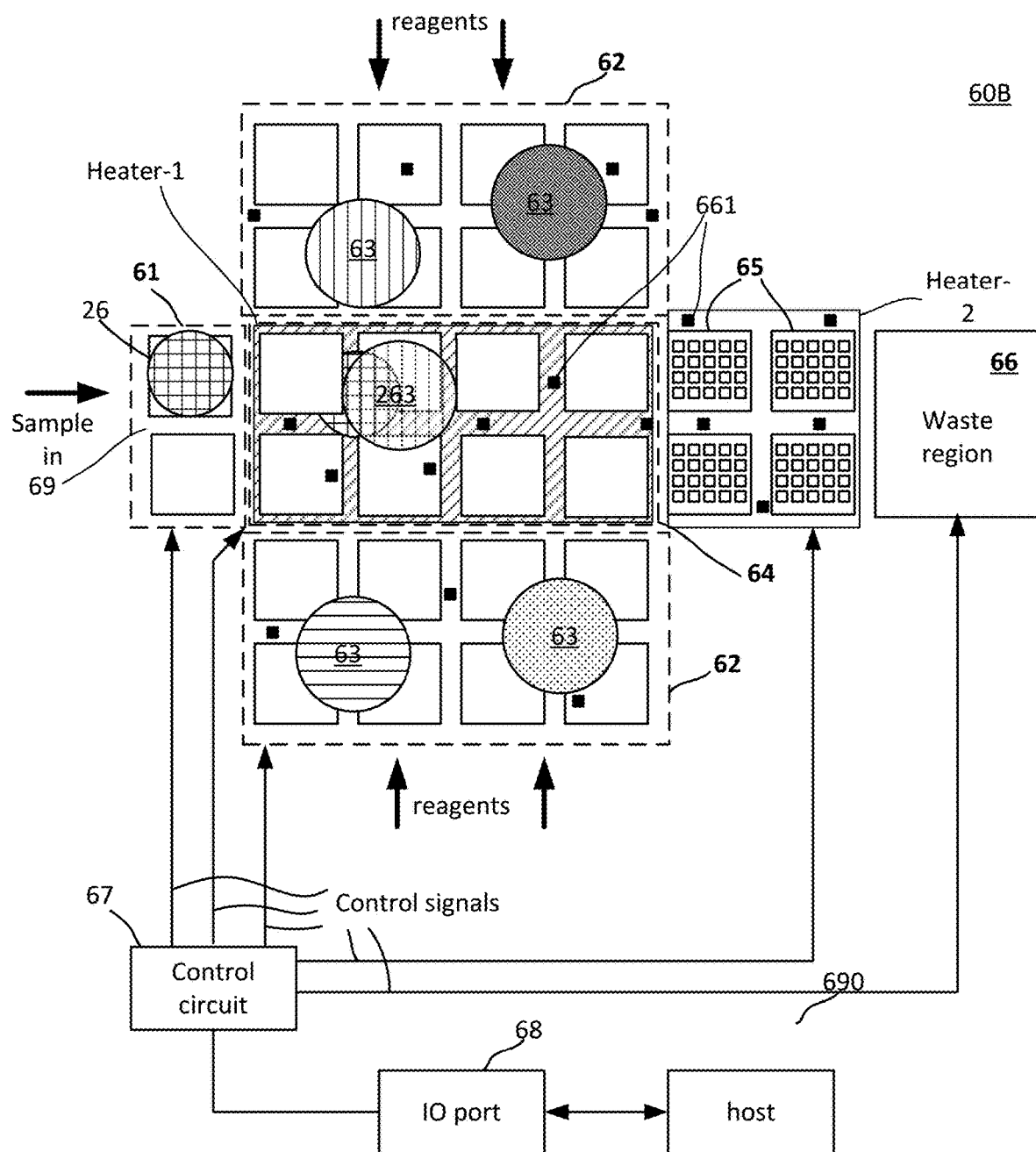
FIG. 6B is a simplified cross-sectional top view of a microfluidic device configured as an integrated lab-on-a-chip device according to an embodiment of the present disclosure.

FIG. 6B is a simplified cross-sectional top view of a microfluidic device configured as an integrated lab-on-a-chip device according to an embodiment of the present disclosure. Referring to FIG. 6B, the integrated lab-on-a-chip device 60B includes a droplet receiving region 61 configured to receive one or more droplets 26, one or more reagent receiving regions 62 configured to receive one or more reagents 63, a mixing region 64 configured to mix the droplet 26 with the one or more reagents 63 to obtain a mixed droplet 263, and a processing region 65 configured to process droplets, for example, partition a droplet (mixed or not mixed) into a plurality of microdroplets and amplify the microdroplets, etc.

Similar to microfluidic device 60A in FIG. 6A, the integrated lab-on-a-chip device 60B in FIG. 6B includes a first substrate structure having a first substrate surface and a second substrate structure having a second substrate surface. These features are not shown in FIG. 6B to simplify the drawing. The second substrate surface faces the first substrate surface and spaced apart from the first substrate surface to form multiple fluid channels for one or more droplets between the first substrate structure and the second substrate structure. The fluid channels can be associated with each region. For example, droplet receiving region 61 is also referred to as the first region and includes a first fluid channel 61', reagent receiving regions 62 are also referred to as the second regions and includes second fluid channels 62', mixing region 64 is also referred to as the third region and includes a third fluid channel 64', and processing region 65 is also referred to as the fourth region and includes a fourth fluid channel 65'. In the top view of FIG. 6B, fluid channels 61', 62', 64', and 65' are disposed in regions 61, 62, 64, and 65, respectively. But the channels 61', 62', 64', and 65' are not marked in FIG. 6B to simply the drawing.

In FIG. 6B, the microfluidic device includes a plurality of regions and multiple fluid channels. A first region including a first fluid channel for receiving a droplet, a second region including a second fluid channel for receiving one or more reagents, a third region in communication with the first region and the second region. The third region configured including a third fluid channel to mix the droplet with the one or more reagents to obtain a mixed droplet. Further, a fourth region is in communication with the third region, and includes a fourth fluid channel and configured to process the mixed droplet. In some embodiments, the fourth region can include a plurality of hydrophilic surface regions spaced apart from one another by hydrophobic surface regions, where a portion of the droplet forms a plurality of microdroplets on the hydrophilic surface regions when the droplet moves over the hydrophilic surface regions. In some embodiments, the fourth region can include a hydrophobic surface region, where droplet processing, such as droplet digital PCR (Polymerase Chain Reaction) can take place.

In some embodiments, the processing region 66 may feature first heating elements configured to heat the microdroplets to a first temperature for a first time duration for amplification of the microdroplets and second heating elements configured to heat the microdrops to a second temperature for a second time duration for annealing the amplified microdroplets. In some cases, the second heating element may be set at a preset constant third temperature. In one embodiment, the lab-on-a-chip device 60 may further include an array of temperature sensors.

In one embodiment, the droplet receiving region 61 may have the device structure shown in FIGS. 1A and 1B. In one embodiment, the reagent receiving region 62 may have the device structure shown in FIGS. 1A and 1B. In other words, the integrated lab-on-a-chip device 60B may be operable to move the one or more droplets and the one or more reagents toward the mixing region 64 and control the mixing of the droplets with the reagents according to a user provided software program. In one embodiment, the processing region 66 may include a plurality of microfluidic devices arranged in a regular pattern, each of the microfluidic devices may have the structure similar or the same as the device structure shown in FIGS. 2A to 2C. The integrated lab-on-a-chip device 60B may further include a waste region 66, also referred to as a waste collection region, for collecting the residual portion of the droplet after the microdroplets have been formed in the processing region and/or the microdroplets after they have been processed and measured. In the example shown in FIG. 6B, two electrodes 69 are used in the droplet receiving regions 61, eight electrodes are used in the upper portion of the reagent receiving region 62, eight electrodes are used in the lower portion of the reagent receiving region 62, eight electrodes are used in the mixing region 64. But it is understood that these number are arbitrary chosen for describing the example embodiment and should not be limiting.

In some embodiments, the integrated lab-on-a-chip device 60B may also include a control circuit 67 configured to provide control signals to the droplet receiving region 61, the reagent receiving region 62, the mixing region 64, the processing region 65, and the waste region 66 for moving the droplet 61, the reagents 63, the mixed droplet 263, the partitioned droplet (i.e., microdroplets), and the residual portion of droplet after passing through the array of processing region. In an embodiment, the integrated lab-on-a-chip device 60B may include an input/output (IO) port 68 configured to interface with a host 690. In one embodiment, the host may be a separate or external processor configured to provide control signals to the integrated lab-on-a-chip device 60. In another embodiment, the host may be integrated with the integrated lab-on-a-chip device 60 in a same package. One of ordinary skill in the art would recognize many variations, modifications, and alternatives. Referring still to FIG. 6B, the control circuit 67 may be disposed remotely from the integrated lab-on-a-chip device 60B and communicates with the integrated lab-on-a-chip device 60B via an input-output port or a serial interface port.

In one embodiment, the integrated lab-on-a-chip device 60B may also include a first heating block "heater-1" formed within the substrate structure below the surface of the mixing regions 64 for maintaining and/or varying an incubation temperature for the mixed droplet 263. In one embodiment, the integrated lab-on-a-chip device 60B may further include a second heating block "heater-2" formed within the substrate structure below the surface of the processing region 65 for maintaining and/or varying an incubation temperature for the microdroplets.

In some embodiments, the first heating block "heater-1" can include a first heating element and a second heating element disposed on either side, respectively, of the second region (mixing region 64) of the fluid channel. The first heating element and the second heating element are similar to the heating elements 640 and 650 illustrated in FIG. 6A, and would be disposed above and below the second region in a cross-sectional view, but are not shown in FIG. 6B to simplify the drawings. Similarly, the second heating block "heater-2" can include a third heating element and a fourth heating element disposed on either side, respectively, of the fourth region (processing region 65) of the fluid channel. The third heating element and the fourth heating element are similar to the heating elements 640 and 650 illustrated in FIG. 6A, and would be disposed above and below the fourth region in a cross-sectional view, but are not shown in FIG. 6B to simplify the drawings.

In some embodiments, the fourth region can have two heating elements sandwiching the fluid channel as described above. However, the second region can have only one heating element disposed below the fluid channel.

In some embodiments, the first heating element and the third heating element are TEC (thermoelectric cooler) Peltier heaters, and the second heating element and the fourth heating element are resistive heaters.

In some embodiments, the first heating element and the third heating element are TEC (thermoelectric cooler) Peltier heaters, and the second heating element and the fourth heating element are TEC (thermoelectric cooler) Peltier heaters.

In some embodiments, the first heating element and the third heating element are resistive heaters, and the second heating element and the fourth heating element are resistive heaters.

In some embodiments, the microfluidic device configured as the integrated lab-on-a-chip device 60B can have has one or more temperature sensors 661 disposed on the first substrate surface in the fluid channel. The microfluidic device can also have a controller 67 configured to monitor temperature measurements provided by the one or more temperature sensors to control at least one of the first heating element and the second heating element. The controller 67 can determine a temperature distribution over the first substrate surface from multiple sensors distributed over the first substrate surface in the fluid channel. In some embodiments, each of the one or more temperature sensors 661 can include an NTC (native temperature coefficient) thermistor. In some embodiments, there can also be one or more temperature sensors disposed on the second substrate surface in the fluid channel.

Alternatively, the first, second, third, and fourth heating elements can be formed of metal or polysilicon wires, metal or polysilicon layer(s), polysilicon layer(s) that can convert an electric energy of signals received from the control circuit 68 into a thermal energy.

In the embodiments described above, each of the first heating block and the second heating clock has two heating element, one above and one below the fluid channel. In some embodiments, the first heating block for the mixing region may have only the bottom heater, and the second heating block for the processing region may have both a top and a bottom heating element.

Figure 7:
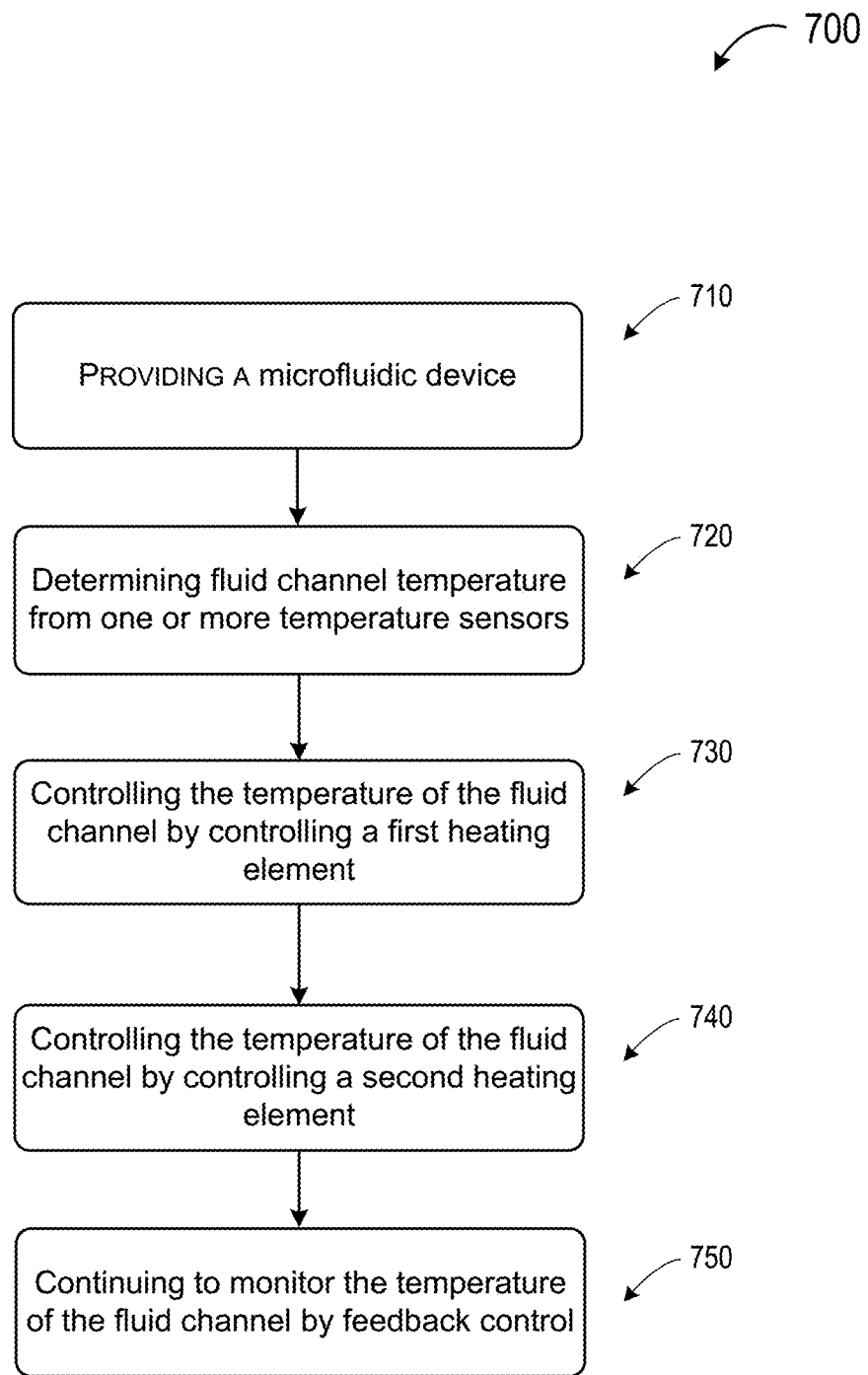
FIG. 7 is a simplified flowchart illustrating a method for forming a plurality of samples from a droplet according to an embodiment of the present disclosure.

FIG. 7 is a simplified flowchart illustrating a method for controlling the temperature of a microfluidic device according to an embodiment of the present disclosure. As shown in FIG. 7, the method 700 includes, at 710, providing a microfluidic device having first substrate structure and a second substrate structure, the first substrate structure having a first substrate surface and the second substrate structure having a second substrate surface, the second substrate surface facing the first substrate surface and spaced apart from the first substrate surface by a distance to form a fluid channel for one or more droplets. Examples of the microfluidic device are described above in connections with FIGS. 4, 5, and 6A-6B.

For example, as shown in FIG. 5, microfluidic device 50 includes a first substrate structure 410 and a second substrate structure 420. The first substrate structure 410 has a first substrate surface 411. In some embodiments, at least a portion of the first substrate surface is hydrophobic. The first substrate surface 411 is configured to receive one or more droplets (not shown). A plurality of electrodes 413 are disposed in the first substrate structure 410 and configured to apply an electric field to the one or more droplets. The second substrate structure 420 has a second substrate surface 421 facing the first substrate surface 411 and spaced apart from the first substrate surface 411 by a distance "d" to define a fluid channel 432 in the space between the first substrate structure 410 and the second substrate structure 420. The distance "d" is configured to contain the one or more droplets disposed in fluid channel 432. In some embodiments, at least a portion of the second substrate surface 421 is hydrophobic.

Microfluidic device 50 also includes a first heating element 440 adjacent to the first substrate structure 410 and disposed on an opposite side of the first substrate surface 411. Microfluidic device 40 also includes a second heating element 450 adjacent to the second substrate structure 420 and disposed on an opposite side of the second substrate surface 421.

At 720, the method 700 includes determining fluid channel temperature from one or more temperature sensors disposed on the first substrate surface. As shown in FIG. 5, microfluidic device 50 can also have a plurality of temperature sensors 460a, 460b, 460c, 460d, 460e, etc. disposed on the first substrate surface 411 in the space between the first substrate structure 410 and the second substrate structure 420. The plurality of temperature sensors can be used to determine the temperature of the fluid channel.

At 730, the method includes controlling the temperature of the fluid channel by controlling a first heating element disposed adjacent to the first substrate surface based on the fluid channel temperature in the fluid channel. As shown in FIG. 5, microfluidic device 50 also includes a first heating element 440 adjacent to the first substrate structure 410 and disposed on an opposite side of the first substrate surface 411. The temperature of the fluid channel is controlled by varying the settings in the first heating element.

At 740, the method includes controlling the temperature of the fluid channel by controlling a second heating element disposed adjacent to the second substrate surface based on the fluid channel temperature in the fluid channel. As shown in FIG. 5, microfluidic device 40 also includes a second heating element 450 adjacent to the second substrate structure 420 and disposed on an opposite side of the second substrate surface 421. The temperature of the fluid channel is controlled by varying the settings in the second heating element. In some embodiments, the top heater is maintained at a constant temperature. In other embodiments, the top heater can be varied in conjunction with the bottom heater to control the temperature of the fluid channel.

At 750, the method 700 includes continuing to monitor the temperature of the fluid channel by feedback control. In some embodiments, microfluidic device 50 can also include a temperature controller 470 configured to monitor temperature measurements provided by the one or more temperature sensors 460 (or 460a-460e, etc.) to control at least one of the first heating element 440 and the second heating element 450. In some embodiments, the controller 470 is configured to determine a temperature distribution over the first substrate surface 411 using the plurality of temperature sensors, 460a-460e, etc., distributed on the first substrate surface.

In some embodiments of the above method, the each of the one or more temperature sensors comprises an NTC (native temperature coefficient) thermistor.

In some embodiments, the first heating element is a TEC (thermoelectric cooler) Peltier heater, and the second heating element is a resistive heater.

In some embodiments, the first heating element is a first TEC (thermoelectric cooler) Peltier heater, and the second heating element is a second TEC (thermoelectric cooler) Peltier heater.

In some embodiments, controlling the temperature of the fluid channel includes:
  controlling the first heating element to heat the fluid channel to a first temperature for a first time duration for droplet amplification;
  controlling the first heating element to heat the fluid channel at a second temperature for a second time duration for droplet annealing; and
  setting the second heating element at a preset constant third temperature.

In some embodiments, each of the one or more temperature sensors comprises an NTC (native temperature coefficient) thermistor.

In some embodiments, the method also includes sensing temperature of the fluid channel using one or more temperature sensors disposed on the second substrate surface in the fluid channel.

In some embodiments, the method also includes a temperature controller configured to monitor temperature measurements provided by the one or more temperature sensors to control at least one of the first heating element and the second heating element.

Figure 8:
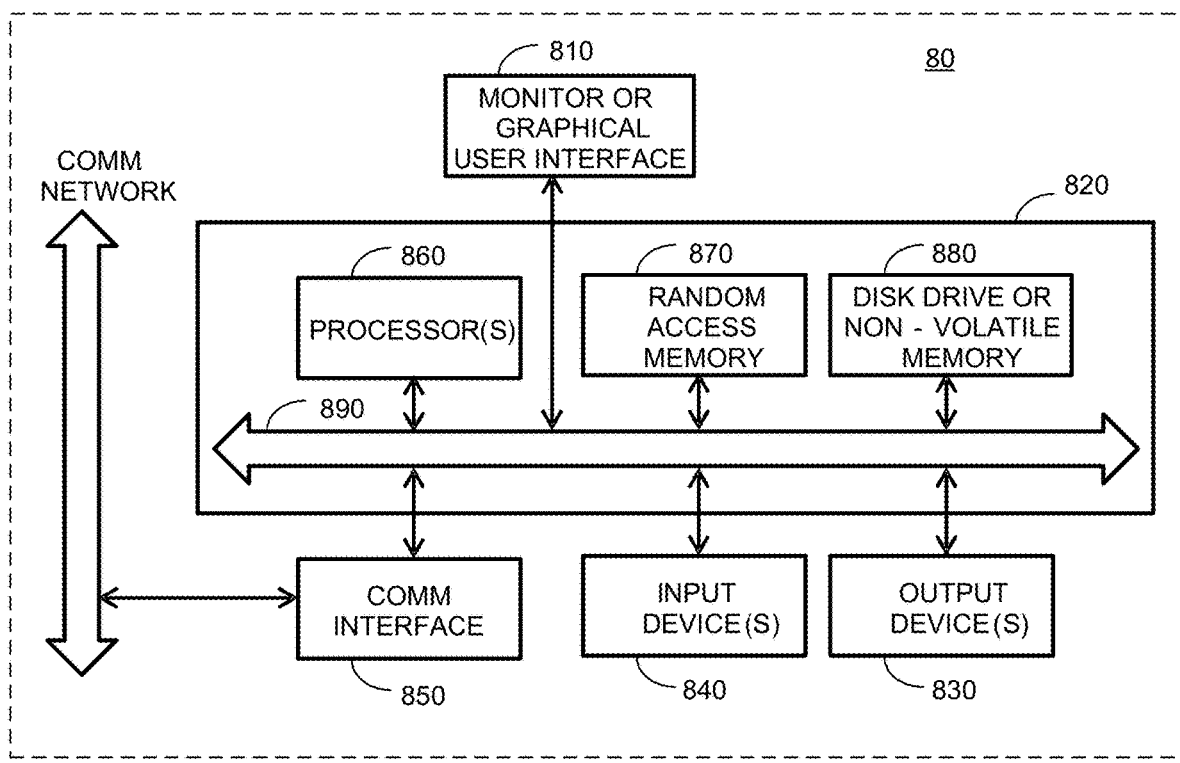
FIG. 8 is a simplified schematic diagram of a computer system that can be used to control the microfluidic device and the lab-on-a-chip device according to an embodiment of the present disclosure.
Figure 8:
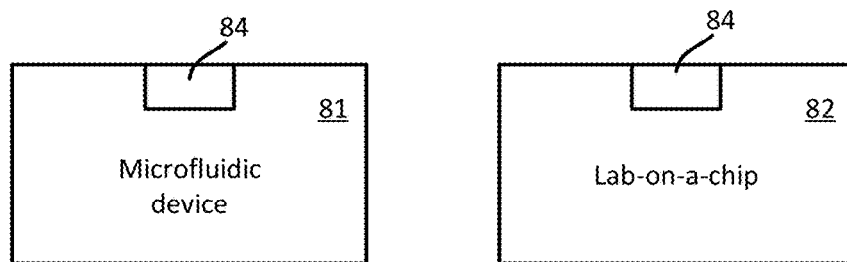

FIG. 8 is a simplified schematic diagram of a mobile computing device 80 that can be used to control microfluidic devices and lab-on-a-chip devices according to an embodiment of the present disclosure. Referring to FIG. 8, the mobile computing device 80 may include a monitor 810, computing electronics 820, user output devices 830, user input devices 840, a communications interface 850, and the like.

The computing electronics 820 may include one or more processors 860 that communicates with a number of peripheral devices via a bus subsystem 890. These peripheral devices may include user output devices 830, user input devices 840, a communications interface 850, and a storage subsystem, such as random access memory (RAM) 870, and a disk drive 880.

The user input devices 830 may include any types of devices and interfaces for inputting information to the computer device 820, e.g., a keyboard, a keypad, a touch screen, a mouse, a trackball, a track pad, a joystick, and other types of input devices.

The user output devices 840 may include any types of devices for outputting information from the computing electronics 820, e.g., a display (e.g., monitor 810).

The communications interface 850 provides an interface to other communication networks and devices. The communications interface 850 may serve as an interface for receiving data from and transmitting data to other systems. For example, the communications interface 850 may include a USB interface for communicating with a microfluidic device or a lab-on-a chip device.

The RAM 870 and the disk drive 880 are examples of tangible media configured to store data such as embodiments of the present disclosure, including executable computer code, human readable code, or the like. Other types of tangible media include floppy disks, removable hard disks, optical storage media such as CD-ROMS, DVDs and bar codes, semiconductor memories such as flash memories, non-transitory read-only-memories (ROMS), battery-backed volatile memories, networked storage devices, and the like. The RAM 870 and the disk drive 880 may be configured to store the basic programming and data constructs that provide the functionality of the present invention.

Software code modules and instructions that provide the functionality of the present disclosure may be stored in the RAM 870 and the disk drive 880. These software modules may be executed by the processors 860.

Referring still to FIG. 8, a microfluidic device 81 and a lab-on-a-chip device 82 each may include an interface port 84 configured to provide communications with the mobile computing device 80. In some embodiments, the mobile computing device 80 may provide instructions and control signals via the interface port 84 to control the signal levels of the electrodes in the microfluidic device 81 and the lab-on-a-chip device 82. In some embodiments, the microfluidic device 81 may include a substrate structure as described in one of the FIGS. 2A-2C, 3A-3C, 4A-4E, 5, and 6A-6B. In some embodiments, the microfluidic device 81 may be part of the lab-on-a chip device 82.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

While the foregoing disclosure shows illustrative aspects of the disclosure, it should be noted that various changes and modifications could be made herein without departing from the scope of the disclosure as defined by the appended claims. The functions, steps and/or actions of the method claims in accordance with the aspects of the disclosure described herein need not be performed in any particular order. Furthermore, although elements of the disclosure may be described or claimed in the singular, the plural is contemplated unless limitation to the singular is explicitly stated.

For all flowcharts herein, it will be understood that many of the steps can be combined, performed in parallel or performed in a different sequence without affecting the functions achieved.

What is claimed is:

1. A microfluidic device, comprising:
   (a) a first substrate structure having a first substrate surface;
   (b) a second substrate structure having a second substrate surface facing the first substrate surface and spaced apart from the first substrate surface to form a fluidic channel for one or more droplets between the first substrate structure and the second substrate structure;
   (c) a plurality of electrodes proximate the fluidic channel configured to move the one or more droplets into a heating zone portion of the fluidic channel by electrowetting;
   (d) a first heating element adjacent the first substrate structure at the heating zone portion;
   (e) a second heating element adjacent the second substrate structure at the heating zone portion;
   (f) a temperature controller configured to control the first and second heating elements, the temperature controller configured to vary an operation state of the first heating element to cycle between different temperatures, the temperature controller configured to maintain the second heating element at a constant temperature as the first heating element cycles between the first and second temperatures; and
   (g) one or more temperature sensors disposed in the fluidic channel in the heating zone portion.

2. The microfluidic device of claim 1, wherein the temperature controller is configured to vary an operation of the first heating element in response to feedback from the one or more temperature sensors.

3. The microfluidic device of claim 1, wherein the first heating element is a Peltier or a resistive heater.

4. The microfluidic device of claim 1, wherein the second heating element is a Peltier or a resistive heater.

5. The microfluidic device of claim 1, wherein the one or more temperature sensors comprises negative temperature coefficient thermistors.

6. The microfluidic device of claim 5, wherein the negative temperature coefficient thermistors are arranged in a sensor array across the heating zone portion.

* * * * *